United States Patent [19]

Schwendemann et al.

[11] 4,455,260

[45] Jun. 19, 1984

[54] PREPARATION OF ALK-1-ENYL ISOCYANATES

[75] Inventors: Volker Schwendemann, Wiesenbach; Karl-Heinz Koenig, Frankenthal, both of Fed. Rep. of Germany

[73] Assignee: BASF Aktiengesellschaft, Ludwigshafen, Fed. Rep. of Germany

[21] Appl. No.: 461,468

[22] Filed: Jan. 27, 1983

[30] Foreign Application Priority Data

Feb. 16, 1982 [DE] Fed. Rep. of Germany ....... 3205433

[51] Int. Cl.³ ................. C07C 118/00; C07C 119/042
[52] U.S. Cl. ........................... 260/453 P; 260/453 AL
[58] Field of Search ...................... 260/453 P, 453 AL

[56] References Cited

U.S. PATENT DOCUMENTS

| | | | |
|---|---|---|---|
| 3,440,268 | 4/1969 | Stamm | 260/453 P |
| 3,862,201 | 1/1975 | Koenig et al. | 260/453 P |
| 4,294,773 | 10/1981 | Koenig et al. | 260/453 P |
| 4,314,948 | 2/1982 | Koenig et al. | 260/453 P |

Primary Examiner—Dolph H. Torrence
Attorney, Agent, or Firm—John H. Shurtleff

[57] ABSTRACT

Alk-1-enyl isocyanates are prepared by reacting a 1-haloalkylcarbamyl halide and/or a 1-haloalkyl isocyanate with a carboxamide, and are useful starting materials for the preparation of pesticides, dyes, drugs, textile water-repellents, detergents, plastics, bleaches and adhesives.

6 Claims, No Drawings

PREPARATION OF ALK-1-ENYL ISOCYANATES

The present invention relates to a process for the preparation of alk-1-enyl isocyanates by reaction of a 1-haloalkylcarbamyl halide and/or a 1-haloalkyl isocyanate with a carboxamide.

It is difficult to synthesize alk-1-enyl isocyanates in an economical manner because these compounds are very reactive, being not only thermally labile but also sensitive to acids and bases and to hydrolysis. The best-known methods of preparation are the Curtius degradation of substituted acrylic acid azides (J. Org. Chem. 26 (1961), 770–779), the pyrolysis of trisvinyl isocyanurates under reduced pressure (German Published Application DAS No. 1,932,811) and the thermal cleavage of N-tert.-alkyl-N-(alk-1-enyl)-carbamyl chlorides (German Published Application DAS No. 1,922,412).

German Laid-Open Application DOS No. 2,937,028 discloses that mixtures of 1-monohalogenated isocyanates and alk-1-enyl isocyanates may be prepared by reacting a 1-haloalkylcarbamyl halide with a relatively high-boiling isocyanate. However, this process has the disadvantage that the alk-1-enyl isocyanates are not obtained in pure form.

German Laid-Open Application DOS No. 2,937,006 discloses that a mixture of a 1-haloalkyl isocyanate and an alk-1-enyl isocyanate may be obtained by reacting a 1-haloalkylcarbamyl halide or a 1-haloalkyl isocyanate with α-pinene. The disadvantage of this process is that the α-pinene undergoes a rearrangement reaction to give bornyl chloride, and hence cannot be regenerated.

We have found that alk-1-enyl isocyanates of the formula

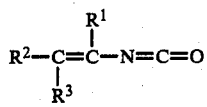

where $R^1$, $R^2$ and $R^3$ may be identical or different and are each hydrogen or methyl, are advantageously obtained if a 1-haloalkylcarbamyl halide of the formula

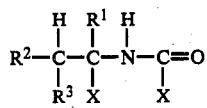

and/or a 1-haloalkyl isocyanate of the formula

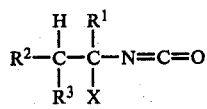

where $R^1$, $R^2$ and $R^3$ have the above meanings and X is halogen, are reacted with a carboxamide of the formula

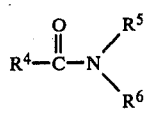

where $R^4$ is hydrogen or an aliphatic or aromatic radical, and $R^5$ and $R^6$ may be identical or different and are each hydrogen or an aliphatic radical, or, together with the adjacent nitrogen atom, are members of a heterocyclic radical.

Where 1-chloroethylcarbamyl chloride and N,N-dimethylacetamide are used, the reaction can be represented by the following equation:

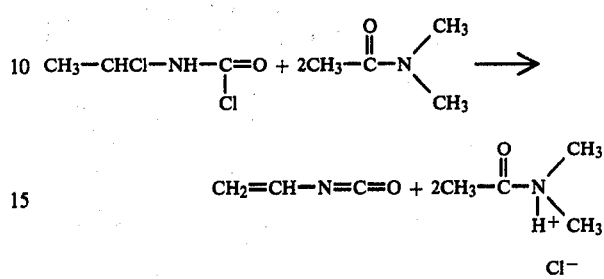

Compared to the prior art, the process according to the invention surprisingly gives alk-1-enyl isocyanates in good yield and purity by a simpler and more economical route. These advantages of the novel process could not be foreseen, since "The Chemistry of Cyanates and their Thioderivatives" (Saul Patai, John Wiley & Sons, New York (1977), page 674) discloses that organic isocyanates, when treated with a base, are readily trimerized with the formation of isocyanurates. Synthesis 1980, page 85, discloses that in α-haloisocyanates the isocyanate function and the α-halogen atom possess further, increased reactivity. It is also surprising that, using a carboxamide IV, it is possible to eliminate hydrogen halide not only at the carbamyl halide group but also at the hydrocarbon chain, an olefinic double bond being formed. The novel process is the more surprising since it is known that alk-1-enyl isocyanates are very sensitive to hydrogen halide, and react with it even at room temperature to form resin-like polymer substances (Recueil 94 (1975), 102), and undergo a spontaneous addition reaction with it at very low temperatures (German Laid-Open Application DOS No. 2,732,284). In view of the carbamyl chloride/isocyanate equilibrium (Houben-Weyl, Methoden der Organischen Chemie, volume 8, page 121), it was to be expected that any alk-1-enyl isocyanate formed would react with hydrogen halide from 1-haloalkylcarbamyl halide which had still not reacted, to give polymeric compounds.

Preferred starting materials II, III and IV, and accordingly preferred end products I, are those of the formulae where the individual radicals X may be identical or different in starting material II, and are each advantageously bromine or, in particular, chlorine, $R^4$ is hydrogen, alkyl of 1 to 12, preferably 1 to 6, carbon atoms or phenyl, and $R^5$ and $R^6$ may be identical or different and are each hydrogen or alkyl of 1 to 6 carbon atoms, or, together with the adjacent nitrogen atom, are members of a 5-membered, 6-membered, 7-membered or 8-membered heterocyclic ring which in addition to the stated nitrogen atom can contain a further nitrogen atom or an oxygen atom. The stated radicals and rings can be further substituted by atoms or groups which are inert under the reaction conditions, e.g. alkyl or alkoxy, each of 1 to 4 carbon atoms, or chlorine, which substitutes the phenyl group. The starting materials II are prepared in a simple manner, for example by the process described in German Laid-Open Application DOS No. 2,741,980.

Examples of suitable starting materials II are 1-chloroethylcarbamyl chloride, 1-bromoethylcarbamyl bromide, 1-chloropropylcarbamyl chloride, 1-bromopropylcarbamyl bromide, 1-chloro-1-methylethylcarbamyl chloride, 1-bromo-1-methylethylcarbamyl bromide, 2-chlorobut-2-ylcarbamyl chloride, 2-bromobut-2-ylcarbamyl bromide, 1-chloro-2-methylpropylcarbamyl chloride, 1-bromo-2-methylpropylcarbamyl bromide, 2-chloro-3-methylbut-2-ylcarbamyl chloride and 2-bromo-3-methylbut-2-ylcarbamyl bromide.

Examples of suitable starting materials III are 1-chloroethyl isocyanate, 1-bromoethyl isocyanate, 1-chloropropyl isocyanate, 1-bromopropyl isocyanate, 1-chloro-1-methylethyl isocyanate, 1-bromo-1-methylethyl isocyanate, 2-chlorobut-2-yl isocyanate, 2-bromobut-2-yl isocyanate, 1-chloro-2-methylpropyl isocyanate, 1-bromo-2-methylpropyl isocyanate, 2-chloro-3-methylbut-2-yl isocyanate and 2-bromo-3-methylbut-2-yl isocyanate.

The reaction is carried out as a rule at from $-10°$ to $150°$ C., preferably from $30°$ to $120°$ C., under atmospheric or superatmospheric pressure, continuously or batchwise. Advantageously, the reaction is started at from $-10°$ to $+30°$ C., the temperature is increased slowly and the reaction is completed at the preferred temperature stated. The reaction time is in general 0.5 to 6 hours.

The amount of starting material IV is advantageously chosen in accordance with the amount of hydrogen halide split off, or with the amount of end product I desired. Thus, it is advantageous to use from 1 to 20, preferably from 2 to 6, moles of carboxamide IV per mole of starting material II, and from 1 to 10, preferably from 1 to 5, moles of carboxamide IV per mole of starting material III.

The reaction is preferably carried out in the absence of a solvent, but it is also possible to use an organic solvent which is inert under the reaction conditions. Examples of suitable solvents are aliphatic and cycloaliphatic hydrocarbons, e.g. pentane, nonane, heptane, octane and cyclohexane, aliphatic halohydrocarbons, e.g. methylene chloride, chloroform, carbon tetrachloride, n-propyl chloride, n-butyl chloride and isomers, amyl chloride, cyclohexyl chloride, ethylidene chloride, dichloroethylene, ethylene chloride, dichloropropane, dichlorobutane, tetrachloromethane, isopropyl bromide, n-propyl bromide, butyl bromide, ethyl iodide and propyl iodide, and fluoro-compounds and partially fluorinated compounds, such as hexyl fluoride and trichlorotrifluoroethane, aromatic hydrocarbons, e.g. benzene, toluene, xylene, ethylbenzene, chlorobenzene, dichlorobenzene, fluorobenzene, difluorobenzene and nitrobenzene, cyclic ethers, e.g. dioxane and tetrahydrofuran, naphthalene derivatives, e.g. chloronaphthalene, ketones, e.g. acetone, methyl ethyl ketone, diethyl ketone and acetophenone, esters, e.g. ethyl formate, methyl acetate, ethyl propionate and methyl phthalate, carbon disulfide, methyl tert.-butyl ether, ethyl propyl ether and acetonitrile, as well as mixtures of such solvents. Chlorobenzene, tetrachloromethane or ethylene chloride is preferably used. Advantageously, the solvent is employed in an amount of from 50 to 10,000, preferably from 50 to 1,000, percent by weight, based on starting material II or III.

The reaction can be carried out as follows: a mixture of starting materials II and/or III and IV is allowed to react at the reaction temperature for the stated time. The end product I is then isolated from the reaction mixture, this advantageously being carried out directly after the reaction by increasing the temperature and distilling. Instead of the pure 1-haloalkyl isocyanate III or 1-haloalkylcarbamyl halide II, it is also possible to use the reaction mixtures from the preparation of these starting materials, for example the crude halogenation mixtures obtained in the halogenation of carbamyl halides.

The alk-1-enyl isocyanates I obtainable according to the invention are useful starting materials for the preparation of pesticides, dyes, drugs, textile water-repellents, detergents, plastics, bleaches and adhesives. Moreover, alk-1-enyl isocyanates are important monomers which can be converted to chain polymers and conductive polymers, for example radiation-curable surface-coating resins (C.A. 51 (1957), 18694 b-e; J. Polym. Sci. 35 (1959), 215-218; and J. Coatings Techn. 49 (1977), part 632, 82-86). They can be converted to urethanes, for example for use as foams or very flexible, high molecular weight coatings, or to ureas. Regarding the use of these compounds, reference may be made to the stated publications and to Ullmanns Encyklopädie der technischen Chemie, 3rd edition, volume 9, pages 11, 12 and 404, and volume 17, page 204.

EXAMPLE 1

348 g of N,N-dimethylacetamide were added dropwise to 142 g of α-chloroethylcarbamyl chloride, the mixture was heated to 40° C. and stirred for 20 minutes, and a solid mixture was obtained. Thereafter, the mixture was heated slowly (in the course of 60 minutes) to 80° C., and the vinyl isocyanate formed was distilled off under 100 mbar. 54.5 g (79% of theory) of vinyl isocyanate having a boiling point of 38°-40° C. and a purity of more than 98% were obtained.

EXAMPLE 2

348 g of N,N-dimethylacetamide were added to 142 g of α-chloroethylcarbamyl chloride in 172 g of chlorobenzene, the mixture was heated to 40° C. and the vinyl isocyanate was then distilled off at 70° C. and under 100 mbar. 57.3 g (83% of theory) of vinyl isocyanate having a boiling point of 38°-40° C. and a purity of more than 98% were obtained.

EXAMPLE 3

348 g of N,N-dimethylacetamide were added dropwise to 231 g of α-bromoethylcarbamyl bromide, the mixture was heated to 40° C. and stirred for 20 minutes, and a solid mixture was obtained. Thereafter, the mixture was heated slowly (in the course of 60 minutes) to 110° C., and the vinyl isocyanate formed was distilled off under 100 mbar. 53.1 g (77% of theory) of vinyl isocyanate having a boiling point of 38°-40° C. and a purity of more than 99% were obtained.

We claim:

1. A process for the preparation of an alk-1-enyl isocyanate of the formula

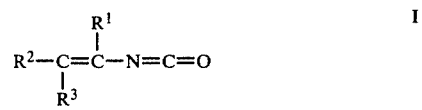

where $R^1$, $R^2$ and $R^3$ may be identical or different and are each hydrogen or methyl, wherein a 1-haloalkylcarbamyl halide of the formula

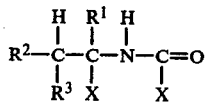

and/or a 1-haloalkyl isocyanate of the formula

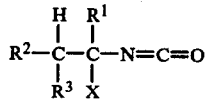

where $R^1$, $R^2$ and $R^3$ have the above meanings and X is halogen, are reacted with a carboxamide of the formula

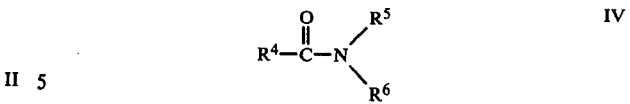

where $R^4$ is hydrogen or an aliphatic or aromatic radical, and $R^5$ and $R^6$ may be identical or different and are each hydrogen or an aliphatic radical, or, together with the adjacent nitrogen atom, are members of a heterocyclic radical.

2. A process as claimed in claim 1, wherein the reaction is carried out using from 1 to 6 moles of carboxamide IV per mole of starting material II.

3. A process as claimed in claim 1, wherein the reaction is carried out using from 1 to 10 moles of carboxamide IV per mole of starting material III.

4. A process as claimed in claim 1, wherein the reaction is carried out at from $-10°$ to 150° C.

5. A process as claimed in claim 1, wherein the reaction is carried out at from 30° to 120° C.

6. A process as claimed in claim 1, wherein the reaction is carried out using an organic solvent which is inert under the reaction conditions, in an amount of from 50 to 10,000 percent by weight, based on starting material II or III.

* * * * *